United States Patent [19]

Sagi

[11] 4,190,058
[45] Feb. 26, 1980

[54] DEVICE FOR USE IN EARLY DETECTION OF BREAST CANCER

[75] Inventor: Zsimond L. Sagi, Denville, N.J.

[73] Assignee: Arden Industries, Inc., Lake Hiawatha, N.J.

[21] Appl. No.: 908,154

[22] Filed: May 22, 1978

[51] Int. Cl.² ............................................. A61B 10/00
[52] U.S. Cl. .................................................... 128/736
[58] Field of Search ........................................ 128/2 H

[56] References Cited

U.S. PATENT DOCUMENTS

| | | | |
|---|---|---|---|
| 3,594,126 | 7/1971 | Fergason et al. | 128/2 H |
| 3,661,142 | 5/1972 | Flam | 128/2 H |
| 4,030,482 | 6/1977 | Navato | 128/2 H |

Primary Examiner—William E. Kamm

[57] ABSTRACT

A device is provided for aid in early detection of breast cancer. The device comprises a flexible, heat-conductive web, preferably in the form of a disc-shaped patch having an adhesive layer on one side thereof and a peelable layer removably secured thereto by said adhesive layer. On the other side thereof, the device comprises an array of spaced-apart indicators, each of said indicators comprising a dye or a pigment and a temperature sensitive substance (crystalline organic chemical) which melts at a relatively precise temperature which is approximately 0.5° F. different from the adjacent indicator. As many indicators are used as are necesary to cover the desired temperature range. The device is incorporated into the breast-receiving cups of a brassiere and mirror image quadrants of the two breasts are scanned and the device is visually examined to determine the number of indicators which have displayed a change in color, thus apprising the person of the existence of abnormality in the mammary tissue.

12 Claims, 4 Drawing Figures

U.S. Patent  Feb. 26, 1980  4,190,058
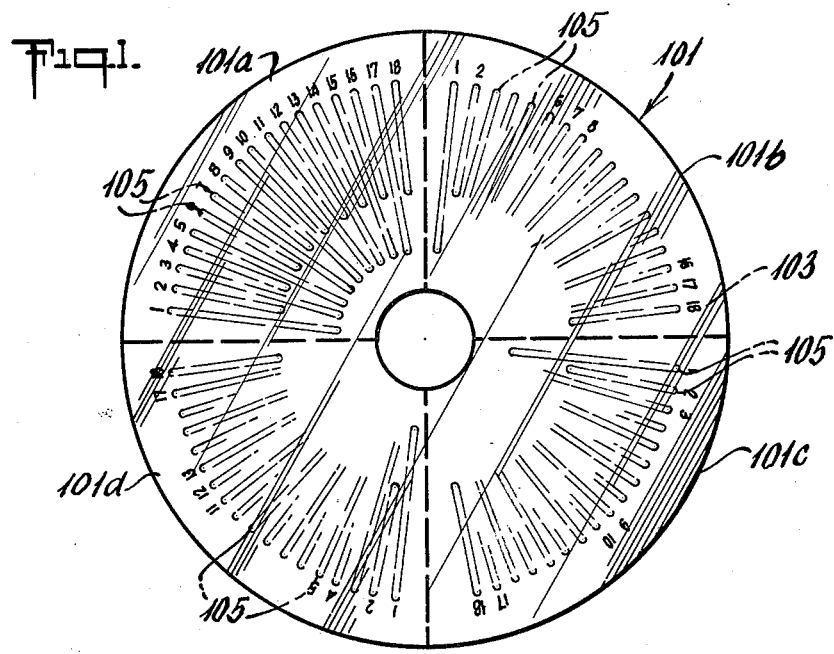
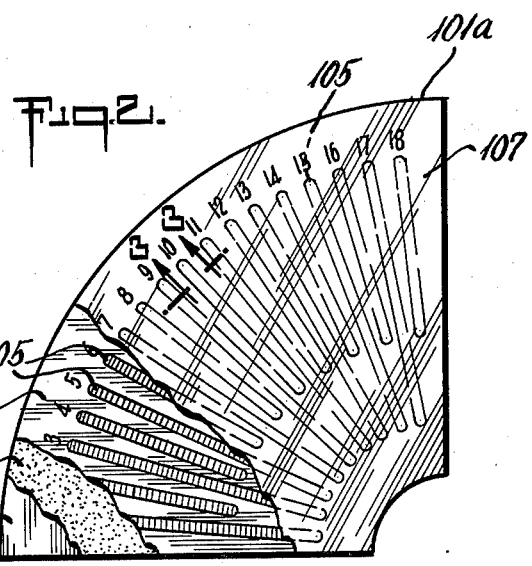
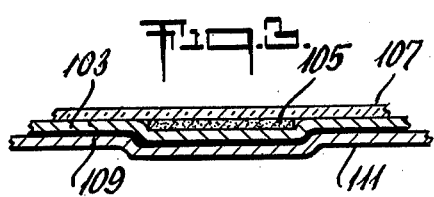 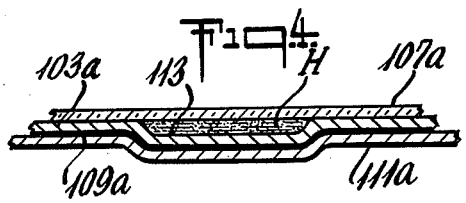

DEVICE FOR USE IN EARLY DETECTION OF BREAST CANCER

Other embodiments of the invention are also described herein.

BACKGROUND OF INVENTION

1. Field of Invention

This invention relates to a device which is useful for early detection of malignant mammary tumors and is particularly related to a device for aid in the visual detection of breast cancer.

2. The Prior Art

Several techniques are currently employed for the detection of malignant tumors in the beast in order to determine if a woman's breast has been afflicted with cancer. As discussed in U.S. Pat. No. 3,847,139, issued on Nov. 12, 1974 to Eric Flam, thermography is, at the present, the technique which is most widely used in medical diagnostics for the detection of breast cancer. Other procedures include physical examination, mammography and xerography.

Physical examination involves probing for lumps or masses in the breast and may be carried out by a physician or the woman herself. The disadvantage of this procedure is that lumps which are large enough to be detected by probing or palpation have often spread far enough to other areas, thus reducing the efficacy of any treatment of the cancerous breast.

Both mammography and xerography involve x-ray examinations by an experienced technician or radiologist. The procedure is time consuming, expensive for the patient and often subjects the patient to repeated radiation dosages which could result in cumulative carciogenic effects.

Thermography is based on infra-red scanning of the surface of the breast and developing a thermogram which contains temperature information corresponding to the scanned surface. Since the temperature of malignant mammary tissues are usually higher than the temperature of normal tissues, the thermogram affords a means by which the presence of localized hot spots can be detected. This technique, however, also involves the use of expensive equipment and expert technicians or radiologists to analyze and interpret the thermogram.

None of the aforementioned techniques lend itself to rapid or simple procedure for early detection of breast cancer and all of them require the patient to visit a physician, a hospital or a clinical center. Frequently, by the time the patient visits the physician or the hospital, the concerous tissues have spread irreversibly and the chance of survival may have considerably diminished.

The aforementioned patent of Flam discloses a device which is intended to aid in early detection of breast caner. The device disclosed by Flam comprises a wastelike structure including a substrate of stretchable, conformable material carrying a temperature responsive coating viewable against the background of the substrate. The temperature responsive coating is a liquid crystal system which reflects the components of incident light. When the device disclosed by Flam is worn by the woman as illustrated in FIG. 1 thereof, the temperature variations over the breast are transferred to the liquid crystal and a thermal pattern of color variations is developed which can be observed by a physician or the woman herself, and may be photographed. A single liquid crystal system with a wide temperature range, corresponding to the skin temperature of the breast of from about 85° F. to 95° F., is used as the temperature responsive coating, or a pair of liquid crystal systems can be used; one liquid crystal system covering the range of from about 85° F. to about 90° F., while the other liquid crystal system covers the range of from about 90° F. to about 95° F.

Another temperature-responsive device for detecting the presence of breast cancer is described by James et al in their U.S. Pat. No. 3,960,138, issued on June 1, 1976. This device is retained in thermal contact with each breast by means of a brassiere, which also contains a differential temperature integrator circuit, whereby the difference in means temperature between the two breasts may be integrated over a period of time.

A temperature-sensing patch is described in another patent (U.S. Pat. No. 3,661,142), granted to Eric Flam on May 9, 1972. The temperature-sensing patch disclosed in this patent comprises a flexible backing web having a pressure-sensitive adhesive coated on one side and a plurality of discrete temperature-sensitive indicators on the other side. Each indicator comprises a layer of encapsulated cholesteric liquid crystals, which contain cholesteric esters such as cholesteryl pelargonate (nonanate), cholesteryl chloride, oleyl cholesteryl carbonate, etc., which have the property of changing color with changes in temperature.

For further discussion of the various methods of detecting breast cancer see the article by Gershen-Cohen et al entitled "Modalities In Breast Cancer Detection Xerography, Mammography, Thermography, And Mammometry," in Cancer, December, 1969, pp. 1226–1230; see also "Advances In Thermography and Mammography," by Gershen-Cohen et al, Annals New York Academy of Sciences (1964), pp. 283–300 and "Relative Densiometric Analysis of Thermograms," by Brueschke et al., Annals New York Academy of Sciences (1964), pp. 82–89.

Notwithstanding the plethora of publications and diligent scientific research in breast cancer detection techology, xerography, mammography and thermography remain today as the principal practical methods which are available for the detection of breast cancer. As it was previously mentioned, however, all of these methods have inherent disadvantages and limitations and, in addition, they are not adapted for quick, initial mass screening which frequently proves to be a matter of life or death for persons at early states of affliction with this disease.

It is, therefore, an object of this invention to provide a device for use in detecting breast cancer.

It is another object of this invention to provide a device for aid in early detection of breast cancer which can be used for self-examination at home.

It is a further object of this invention to provide a breast cancer detection device which is relatively simple to use, and which does not require complicated and expensive equipment or experienced technicians or radiologists to interpret the results obtained thereby.

The foregoing and other objects of this invention will become more apparent from the following detailed description of the invention and the accompanying drawings.

SUMMARY OF INVENTION

In accordance with this invention, a device is provided for aiding in early detection of breast cancer. The device, which is adapted for home use, comprises a flexible, heat-conductive web, preferably in the form of a disc-shaped patch having an adhesive layer on one side thereof and a pealable layer removably secured thereto by means of said adhesive layer.

In one embodiment of the invention, the disc-shaped patch is cut out into four generally pie-shaped segments which, for convenience, will be referred to as "quadrants". On its other side, each quadrant comprises an array of spaced-apart and preferably radially-disposed indicators which are identified by corresponding array of indicia. Each indicator comprises a dye or a pigment and a temperature sensitive substance which is capable of melting at a relatively precise temperature, and wherein the melting point of each of said temperature-sensitive substances is approximately 0.5° F. different from the melting point of the temperature-sensitive substance in the adjacent-indicator. Thus, as many indicators are used as are necessary to cover the desired temperature range.

The device is used by incorporating it into the breast-receiving cups of the brassiere such that the indicators are in contact with the surface of the breast. After few minutes, the device is visually examined and mirror image quadrants are compared to determine the number of indicators which have displayed color change. A change in color of at least two more indicators in any quadrant, as compared to its mirror image quadrant, indicates possible abnormality of the mammary tissues in that quadrant requiring consultation with a physician and a more detailed examination.

Different embodiments of this invention are described in the detailed description of the invention.

BRIEF DESCRIPTION OF DRAWINGS

FIG. 1 is a plan view of the device of this invention;

FIG. 2 is a plan view of a quadrant of the device shown in FIG. 1;

FIG. 3 is a sectional view taken along the line 3—3 in FIG. 2; and

FIG. 4 is a sectional view similar to FIG. 3 but illustrating a different embodiment of this invention.

DETAILED DESCRIPTION OF INVENTION

It is well known that the average difference in surface temperature of the breasts is larger for persons with a malignant tumors in one breast than those having normal (non-malignant) breasts. Moreover, the temperature difference in malignant mammary tumors is usually more than 1° C. (1.3° F.), and is invariably more than 0.6° C. (1.08° F.). Also, while the temperature of a normal breast tends to fluctuate, the temperature of a malignant breast remains relatively constant, and at a higher temperature than the temperature of the normal breast.

This invention is predicated upon the discovery that such differences in temperature between malignant and non-malignant breasts can be detected—and visually displayed—by means of a novel and unique device which is characterized by its simplicity and reliability for aiding in early detection fo breast cancer. Simplicity of its use makes the device of this invention readily adaptable for mass screening and affords a rapid means whereby a person can determine if she (or he) is afflicted with breast cancer before undergoing a more comprehensive examination by a physician by means of xerography, thermography or mammography.

Referring now to the drawings wherein like reference numerals are employed to designate like parts, the device is shown in FIG. 1 in the form of a disc-shaped patch 101 comprising a flexible, conformable heat-conductive material 103 which may conveniently and preferably be an aluminum foil having a thickness of from about 1 to about 3 mils. The disc-shaped patch 101 may be made in various convenient sizes ranging from about 5 inches to about 7 inches in diameter for insertion into the breast-receiving cups of a brassiere as will hereinafter be described. The patch 101 consists of four generally pie-shaped segments 101a, 101b, 101c and 101d which are essentially identical in sizes and configurations, and which, for convenience, will be referred to as quadrants, with each quadrant comprising an array of radially disposed, spaced apart indicators 105. Eighteen indicators are shown in each quadrant, with each indicator adapted to display a visual change in color corresponding to a predetermined temperature.

In the embodiment illustrated in FIGS. 1 and 2, the indicators are identified by a plurality of adjacent indicia ranging from 1 to 18, corresponding to the temperature range of 89° to 97.5° F., in 0.5° F. gradations, as follows:

| Indicator No. | Corresponding Temperature, °F. |
|---|---|
| 1 | 89 |
| 2 | 89.5 |
| 3 | 90 |
| 4 | 90.5 |
| 5 | 91 |
| 6 | 91.5 |
| 7 | 92 |
| 8 | 92.5 |
| 9 | 93 |
| 10 | 93.5 |
| 11 | 94 |
| 12 | 94.5 |
| 13 | 95 |
| 14 | 95.5 |
| 15 | 96 |
| 16 | 96.5 |
| 17 | 97 |
| 18 | 97.5 |

The number of indicators as well as the temperature range and temperature gradations may vary, however, for breast cancer detection, and using the device illustrated in FIGS. 1 and 2, eighteen indicators per quadrant covering the aforementioned temperature range, in 0.5° F. gradations, are quite satisfactory.

The indicators 105 are formed as follows: Specially manufactured paper available from the National Cash Register, Dayton, Ohio, is precut into as many strips as are needed for each patch. For the embodiment illustrated in FIG. 1, eighteen such indicator strips are shown in each quadrant. The length and width of the indicator strips are not, per se, critical and usually, they are precut to suitable dimensions so that eighteen such indicator strips may be spaced apart radially, in each quadrant of the patch.

The specially treated indicator paper which comprises a dye or a pigment, or any other indicator paper which may be treated with a suitable dye or pigment, is then treated (e.g., impregnated) with a thermally-responsive, temperature-sensitive substance which melts at a relatively precise temperature ranging from 89° F. to 97.5° F. A host of chemical compounds naturally suggest themselves for this application and are available from a variety of sources. It is important to note, however, that in the practice of this invention, each indicator strip comprises a substance or chemical which not only melts at one of the aforesaid temperature range, but its melting point must be approximately 0.5° F. different from the melting point of the chemical in the next indicator. Thus, the indicator strip corresponding to the numeral 1 comprises a chemical which melts at 89.0° F., the indicator corresponding to the numeral 2 comprises a chemical which melts at 89.5° F. and so on, until the indicator which is designated by the numeral 20 which comprises a substance which melts at 97.5° F.

The chemicals employed in the practice of this invention are preferably crystalline organic chemicals with relatively precise and sharp melting points at the aforementioned temperature range but which recrystallize upon standing at ambient temperatures (room temperature).

The indicator strips 105, after treatment and impregnation with a dye or a pigment and the temperature-sensitive substance as aforesaid, are printed, embossed or otherwise suitably arrayed on the patch 101 as previously described and the patch is then covered with a flexible, transparent plastic layer 107 such as Mylar, Nylon, Surlyn, etc., and heat sealed. Thus, referring now to FIG. 3, the underside of the aluminum foil 103 is provided with an adhesive layer 109, and a pealable release paper 111 which is adhesively secured to the aluminum foil, but which is pealable therefrom before use.

In use, release paper 111 is removed from the pre-cut pie-shaped segments or quadrants, and the quadrants are inserted into the breast-receiving cups of the brassiere such that the adhesive surface is secured to the inside surface of the brassiere and the other side, i.e., the side comprising the indicator strips 105 is in conformable contact with the breast surface. Mirror image sections or quadrants of the breasts are thus scanned, and after few minutes, the brassiere is removed and each patch is visually examined by comparing the number of indicator strips in mirror image quadrants which have displayed a change in color due to melting of the temperature sensitive chemicals used therein. The change in color is either from white to blue or vice-versa depending on the chemicals and dyes which are employed although the exact color may be different for other chemicals or dyes. If at least two or more indicators in one quadrant of, say the left breast, have displayed a change in color as compared to the mirror image quadrant on the right breast, the person is warned of abnormalities in the mammary tissues in that quadrant of the left breast, and possible affliction with cancer which warrants consulting a physician for more detailed examination.

Since this test is relatively simple to perform and does not require any expertise or complicated equipment, it may be repeated two or three times to confirm the initial observations.

Numerous advantages become immediately apparent from the foregoing description of the invention. The test may be performed at home and as frequently as desired without visiting a physician or a clinical center.

While the invention has heretofore been described with a certain degree of particularity, naturally, some changes and modifications may be made therein which are nevertheless within the scope of this invention. For example, and instead of using chemically-impregnated indicator papers comprising a dye or a pigment, the chemical and the dye may be pre-mixed and then deposited as an array of spaced-apart radially disposed indicators much in the form of indicator strips 105 as shown in FIG. 1. The mixture of chemical and the dye (or pigment) is thus imprinted on the disc-shaped patch 101 such that a sectional view thereof is as illustrated in FIG. 4.

Referring now to FIG. 4, there is shown the aluminum foil 103a which may be slightly indented as in 113, shown in exaggerated dimensions. As in the embodiment shown in FIG. 3, the aluminum foil 103a is provided with an adhesive underlayer 109a and a release paper 111a which is pealably adhered to the aluminum foil.

The temperature sensitive material H (a mixture of chemical and a dye or a pigment) is deposited in the indented area 113 and a transparent plastic layer 107a, e.g., Mylar, Nylon, or Surlyn overlies the top surfaces of the aluminum foil and is heat sealed thereto.

In the embodiment shown in FIG. 3, when the disc-shaped patch is used to scan the surface of the breast as hereinbefore described, all chemicals melt at their respective melting points thus displaying a visible change in color. The number of indicators which have displayed a change in color are compared in mirror image quadrants of the two breast as previously described in order to determine if there is any abnormality in the mammary tissues.

Also, while the device is shown in FIGS. 1 and 2 in the form of a disc-shaped member and a pie-shaped segment, respectively, these configurations may vary somewhat without changing the underlying inventive concept. Additionally, more than four quadrants or segments may be used to scan each breast so long as mirror image segments of the breasts are compared as aforesaid. However, and as a matter of convenience, the device shown in FIGS. 1 and 2 is more practical since it may be sized to conformably cover the breast area.

Other embodiments suggest themselves from the foregoing detailed description which are nevertheless within the scope and spirit of this invention.

What is claimed:

1. A device for use in early detection of breast cancer, which device comprises:
    (a) a flexible, heat-conductive web,
    (b) an adhesive layer on one side of said web and a pealable layer removably adhered to said web by said adhesive layer,
    (c) an array of spaced-apart indicators on the other side of said web, each of said indicators comprising a dye or a pigment and a temperature-sensitive substance having a relatively precise melting point approximately 0.5° F. different from the melting point of the temperature-sensitive substance in the adjacent indicator, and wherein each indicator displays a change in color upon melting of each of said temperature sensitive substance, and
    (d) a transparent flexible layer conformably overlying said web and sealably secured thereto for visual examination of the change in color of said indicators.

2. A device as in claim 1 wherein said web is made of an aluminum foil.

3. A device as in claim 2 wherein each of said temperature-sensitive substances is a crystalline organic chemical.

4. A device as in claim 3 wherein said device is generally circular in configuration and wherein said indicators are radially disposed thereon.

5. A device as in claim 3 wherein said device is generally pie-shaped in configuration and wherein said indicators are radially disposed thereon.

6. A device as in claim 2 wherein said device is generally circular in configuration and wherein said indicators are radially disposed thereon.

7. A device as in claim 2 wherein said device is generally pie-shaped in configuration and wherein said indicators are radially disposed thereon.

8. A device as in claim 1 wherein each of said temperature-sensitive substances is a crystalline organic chemical.

9. A device as in claim 8 wherein said device is generally circular in configuration and wherein said indicators are radially disposed thereon.

10. A device as in claim 8 wherein said device is generally pie-shaped in configuration and wherein said indicators are radially disposed thereon.

11. A device as in claim 1 wherein said device is generally circular in configuration and wherein said indicators are radially disposed thereon.

12. A device as in claim 1 wherein said device is generally pie-shaped in configuration and wherein said indicators are radially disposed thereon.

* * * * *